United States Patent
Li et al.

(10) Patent No.: US 9,290,620 B2
(45) Date of Patent: Mar. 22, 2016

(54) PRODUCTION AND COMPOSITION OF GLYCEROL BASED POLYOLS

(75) Inventors: Xiaojin Harry Li, Palatine, IL (US); Joanna L. Shih, Downers Grove, IL (US); Heinrich E. Bode, Aurora, IL (US); Jing Wang, Aurora, IL (US); Frederick J. Swiecinski, Algonquin, IL (US)

(73) Assignee: NALCO COMPANY, Naperville, IL (US)

(*) Notice: Subject to any disclaimer, the term of this patent is extended or adjusted under 35 U.S.C. 154(b) by 642 days.

(21) Appl. No.: 12/582,827

(22) Filed: Oct. 21, 2009

(65) Prior Publication Data

US 2011/0092743 A1    Apr. 21, 2011

(51) Int. Cl.
| | |
|---|---|
| C07C 41/18 | (2006.01) |
| C08G 65/34 | (2006.01) |
| C07C 41/09 | (2006.01) |
| C07C 51/41 | (2006.01) |

(52) U.S. Cl.
CPC .............. C08G 65/34 (2013.01); C07C 41/09 (2013.01); C07C 51/41 (2013.01)

(58) Field of Classification Search
None
See application file for complete search history.

(56) References Cited

U.S. PATENT DOCUMENTS

| | | | |
|---|---|---|---|
| 2,258,892 A | 10/1941 | Harris | |
| 3,637,774 A | 1/1972 | Babayan et al. | |
| 4,551,561 A | 11/1985 | Sthuler | |
| 5,198,532 A | 3/1993 | Blytas et al. | |
| 5,399,371 A * | 3/1995 | Harris | 426/611 |
| 5,641,816 A | 6/1997 | Klein et al. | |
| 5,756,639 A * | 5/1998 | Blytas et al. | 528/110 |
| 6,620,904 B2 | 9/2003 | Lemke | |
| 6,822,068 B2 | 11/2004 | Sunder et al. | |
| 2002/0058781 A1 | 5/2002 | Lemke | |
| 2008/0282579 A1 | 11/2008 | Bobbett et al. | |
| 2008/0306211 A1 | 12/2008 | Lemke et al. | |
| 2009/0082483 A1 | 3/2009 | Petrovic et al. | |
| 2009/0130006 A1 | 5/2009 | Wang et al. | |

FOREIGN PATENT DOCUMENTS

| | | |
|---|---|---|
| CN | 101189996 A | 5/2008 |
| EP | 0719752 B1 | 3/2008 |
| JP | 3717193 | 11/1995 |
| WO | WO 2007/049950 A2 | 5/2007 |

OTHER PUBLICATIONS

Janssen et al. (Applied and Environmental Microbiology, Mar. 2007, vol. 73, No. 5, pp. 1601-1611).*

(Continued)

*Primary Examiner* — Rosalynd Keys
(74) *Attorney, Agent, or Firm* — Eric D. Babych; Brinks Gilson & Lione

(57) ABSTRACT

The invention provides a method of efficiently producing branched, cyclic glycerol-based polyols with a co-product as anti-biodegrading agent from inexpensive readily available glycerol monomer. The method involves polymerizing glycerol or glycerol with at least another monomer to multiple other monomers in the presence of particular amount of a strong base as the catalyst under a particular distillation environment. The polyol produced by the inventive method is beneficial of reducing scales in Bayer liquid for aluminum production process and improving brightness of coated paper substrates without greening effect.

19 Claims, 2 Drawing Sheets

(56) References Cited

OTHER PUBLICATIONS

Kishida et al., "Conversion of Glycerin into Lactic Acid by Alkaline Hydrothermal Reaction", Chemistry Letters, vol. 34, No. 11, 2005, pp. 1560-1561).*

Jabeera et al. "The synergistic inhibitive effect of tungstate with zinc ions on the corrosion of iron in aqueous environments, "*Anti-Corrosion Methods and Materials*, vol. 49, No. 6, 2002, pp. 408-416.

G. Odion, *Principles of Polymerization, 4$^{th}$ Edition*, Wiley-InterScience, 2004, Introduction, pp. 18-25.

A. Sunder et al., "Controlled Synthesis of Hyperbranched Polyglycerols by Ring-Opening Multibranching Polymerization," *Macromolecules*, 1999, vol. 32, p. 4240.

D.A. Zhukov et al. "Determination of the Optimum Conditions for the Condensation of Glycerin in the Presence of Potassium Hydroxide," *Zhurnal Prikladoni Khimii*, 1984, vol. 57, No. 2, pp. 389-392.

Kishida et al. "Conversion of Glycerin into Lactic Acid by Alkaline Hydrothermal Reaction" Chemistry Letters 2005 34(11):1560-1561.

* cited by examiner

PRODUCTION AND COMPOSITION OF GLYCEROL BASED POLYOLS

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

This invention relates to methods of producing a unique composition of glycerol-based polyol products. The unique glycerol-based polyol products include branched, cyclic polyols and a beneficial co-product lactic acid and/or lactate salt as an anti-biodegrading agent. Glycerol-based polyols include polyglycerols, polyglycerol derivatives and a polymer consisting of glycerol units and at least another monomer units to other multiple monomers units. The molecular weight of glycerol-based polyols produced through the improved methods can be preferentially high but also can be low as needed.

Glycidol-based synthesis is particularly useful in producing structured or hyperbranched polyglycerols (HBPG) and high molecular weight HBPG, such as those described in U.S. Pat. No. 6,822,068 B2 and US Published Application 2008/282579 A1. Unfortunately these syntheses rely on expensive monomer glycidol which is often so expensive that in many cases their use on an industrial scale is cost prohibitive.

A number of production processes have been developed for synthesis of glycerol-based polyols, particularly polyglycerols, from inexpensive monomer glycerol. However, these syntheses are mostly limited to producing linear or at least mostly linear, low molecular weight polyglycerols (or oligoglycerols). U.S. Pat. No. 2,258,892 describes various reaction conditions for synthesizing polyglycerols at reaction temperature 200 to 260 degrees Celsius employing 1% of a caustic or salt by weight as the catalyst relative to glycerol used, but only oligomeric polyglycerol products were produced (mean molecular weight: 116 to 314 Daltons). In U.S. Pat. No. 5,641,816 0.12% of LiOH or lithium soaps under nitrogen atmosphere were used. In U.S. Pat. No. 6,620,904 B2 0.1% of calcium hydroxide under vacuum was used. In WO 2007/049950 A2 1% of a weak acid alkaline metal salt was used. In each of these cases, however, only oligomeric polyglycerols were produced.

Another strategy used in the prior art is the use of small amounts of strong bases. In EP 0719752 B1 1% of sodium hydroxide under vacuum or nitrogen was used. JP 3717193 describes using 0.5% of sodium hydroxide under nitrogen. US Application 2008/306211 A1 describes using 0.3% or 0.4% of KOH. Again however the only major product was oligomeric polyglycerols or olygomeric glycerol-based polyols. Other methods are described in U.S. Pat. Nos. 3,637,774, 4,551,561, and 5,198,532, Chinese Patent Application CN 101186696A and Scientific Article *Determination of the Optimum Conditions for the Condensation of Glycerin in the Presence of Potassium Hydroxide*, D. A. Zhukov, et al., Zhumal Prikladoni Khimii, Vol. 57, No. 2, pp. 389-392 (1984). Unfortunately these methods also only produce linear polyglycerols with no branching or cyclized structures.

Although glycerol is not expensive, the current processes for the glycerol-based condensation polymerizations are often inefficient. The resulting polyols are linear and often have rather low molecular weights, mostly less than 1000 Daltons. In addition these prior art methods lack any anti-biodegrading agents. Thus there is a clear need for and utility in an improved method of synthesizing polyglycerols and other glycerol-based polyols. The art described in this section is not intended to constitute an admission that any patent, publication or other information referred to herein is "prior art" with respect to this invention, unless specifically designated as such. In addition, this section should not be construed to mean that a search has been made or that no other pertinent information as defined in 37 C.F.R. §1.56(a) exists.

BRIEF SUMMARY OF THE INVENTION

At least one embodiment of the invention is directed towards a method of synthesizing glycerol-based polyol products. The method comprises the step of: reacting a reaction mass comprising at least glycerol monomer in the presence of a strong base catalyst of a concentration above 2%, in a low reactivity atmospheric environment at a temperature above 200 degrees C. which produces a product comprising branched, cyclic polyols and a co-product comprising lactic acid, lactic salt, and any combination thereof. The method can further comprise the steps of providing a catalyst above 3%. The catalyst may be selected from the group consisting of: NaOH, KOH, CsOH, a base stronger than NaOH, and any combination thereof. The strong base catalyst in the particular amount can be used with combining a base weaker than NaOH. The atmospheric environment may be an atmospheric pressure of less than 760 mm Hg and/or may be a flow of an inert gas selected from the list of $N_2$, $CO_2$, He, other inert gases and any combination thereof and the flow is at a rate of 0.2 to 15 mol of inert gas per hour per mol of monomer. The particular atmospheric environment profile applied can be stead, gradual increase, gradual decrease or any combination thereof.

The method may produce glycerol-based polyol products are selected from the group consisting of polyglycerols, polyglycerol derivatives, a polyol having both glycerol monomer units and non-glycerol monomer units and any combination thereof. The glycerol-based polyols products have at least two hydroxyl groups. At least a portion of the produced polyols may have both at least a 0.1 degree of branching and at least a 0.01 degree of cyclization. The co-product may be at least 1% by weight. The glycerol-based polyol products may be at least 166 Daltons in molecular weight. The glycerol-based polyol products may have a polydispersity of at least 1.

The method may make use of different forms of glycerol including pure, technical, crude, or any combination thereof. The method may further comprise other monomers selected from the group consisting of polyols such as pentaerythritol and glycols, amines, other monomers capable of reacting with glycerol or glycerol-based polyol intermediates and any combination thereof. The monomer(s) and/or catalyst (s) can be mixed at the very beginning of the reaction, at any time during the reaction and any combination thereof. The glycerol-based polyol products may be resistant to biological contamination for at least two years after synthesis. The method may further comprise the steps of pre-determining the desired molecular weight of the produced polyglycerol and adjusting the atmospheric environment to match the environment optimum for producing the desired molecular weight. The method may further comprise the steps of pre-determining the desired degree of branching and the desired degree of cyclization of the produced polyglycerol and the desired amount of co-product, and adjusting the atmospheric environment to match the environment optimum for producing the desired degree of branching, degree of cyclization and amount of co-product lactic acid and/or lactate salt. The branched, cyclic polyols may be in molecular weight range of 2,240 to 150,000 Daltons and have a polydispersity range of 1 to 30.

BRIEF DESCRIPTION OF THE DRAWINGS

A detailed description of the invention is hereafter described with specific reference being made to the drawings in which.

DETAILED DESCRIPTION OF THE INVENTION

Definitions

For purposes of this application the definition of these terms is as follows:

"Glycerol-based polyols" means any polymers containing repeating glycerol monomer units such as polyglycerols, polyglycerol derivatives, and a polymer consisting of glycerol monomer units and at least another monomer units to other multiple monomers units regardless of the sequence of monomers unit arrangements. These polymers also comprise at least two or multiple free hydroxyl groups.

Figure 1:
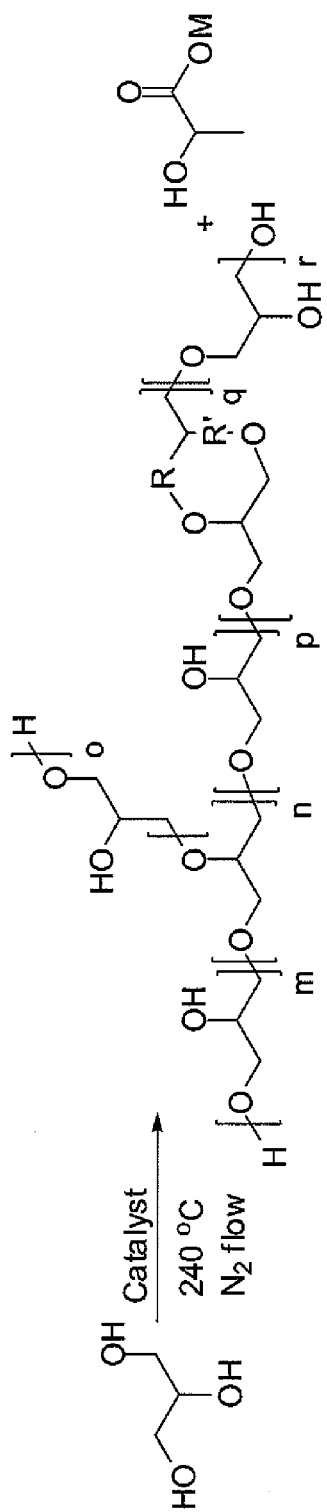
FIG. 1 is an illustration of an inventive polymerization reaction.

"Degree of Branching" or DB means the mol fraction of monomer units at the base of a chain branching away from the main polymer chain relative to a perfectly branched dendrimer, determined by $^{13}$C NMR based on known literature method described in *Macromolecules*, 1999, 32, 4240. Cyclic units are not included in the degree of branching. In a perfect dendrimer the DB is 1 or 100%. FIG. 1 illustrates a compound with a DB of $\frac{1}{7}$.

"Hyperbranched" means a polymer, which is highly branched with three-dimensional tree-like structures or dendritic architecture.

"Degree of cyclization" or DC means the mol fraction of cyclic structure units relative to the total monomer units in a polymer. The cyclic structure units can be formed by intramolecular cyclization of the polyols or any other ways to incorporate in the polyols. The cyclic structure units comprise basic structure units (V, VI and VII of FIG. 2) and the analogues thereof. The degree of cyclization may be determined by $^{13}$C NMR.

"Low reactivity atmospheric environment" is an atmospheric environment which is less reactive than the standard earth environment, which is achieved by substituting the atmospheric environment with an inert gas such as nitrogen, $CO_2$, He, and any combination thereof, or by reducing the atmospheric pressure to less than 760 mm Hg.

"Solids" means all starting materials used in the reaction except for solvents and water. Solids, includes but is not limited to products, co-products or by-products and any starting materials.

In the event that the above definitions or a definition stated elsewhere in this application is inconsistent with a meaning (explicit or implicit) which is commonly used, in a dictionary, or stated in a source incorporated by reference into this application, the application and the claim terms in particular are understood to be construed according to the definition in this application, and not according to the common definition, dictionary definition, or the definition that was incorporated by reference.

Figure 2:
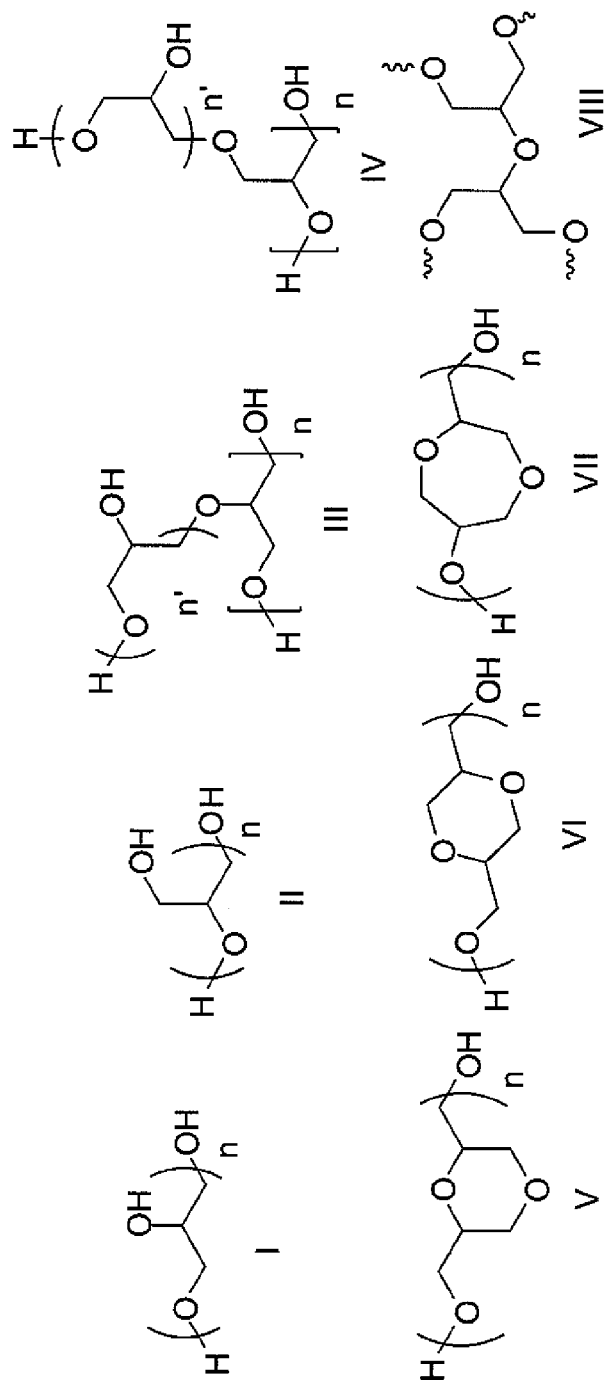
FIG. 2 is an illustration of basic structural units useful with the inventive polymerization reaction.

As illustrated in FIG. 1, in at least one embodiment, a unique composition of glycerol-based polyol is produced from glycerol using an improved method. The polyol comprises a structure including at least two repeating units selecting from at least one of the structures listed in FIG. 2 including but not limited to structures I and II, branched structures III, IV, and VIII, cyclic structures V, VI, VII and any combination thereof. Any structure in FIG. 2 can be combined with any structure or structures including itself through any free hydroxyl group functionality in the structure. The cyclic linkages of any basic cyclic structures in FIG. 2 may contain any structure or structures as a part or parts of linkages. In FIG. 1 and FIG. 2 the numbers m, n, n', o, p, q and r in each structure can independently be any numeric number 0, 1, 2, ... m ... or r. In FIG. 1 R and R' are $(CH_2)_n$ and n can independently be 1 or 0, and M can be H, metal or other counterion.

In at least one embodiment, a unique composition of glycerol-based polyol is produced from glycerol and at least one or more other monomers. Suitable monomers are any polyols or hydrogen active compounds such as those described in U.S. Pat. No. 6,822,068 B2, such as pentaerythrital, glycols, amines, etc. capable of reacting with glycerol or any polyglycerol structures.

In at least one embodiment the unique compositions of glycerol-based polyol products produced by the improved method comprise branched, cyclized structure units in the polyol and co-product lactic acid or lactate salt. In at least one embodiment the glycerol-based polyols have at least 0.1 of degree of branching, preferentially from 0.2 to 0.5, and a degree of cyclization at least 0.01, preferentially 0.02 to 0.19. In at least one embodiment the valuable co-product lactic acid or and lactate salt produced in the invention is at least 1%, preferentially 5% to 30%, by weight in the product solids. The produced lactic acid or lactic salt is particularly useful as it protects the glycerol-based polyols from bacterial and fungal spoilage. Biochallenge experimental tests show that the polyglycerols products are not susceptible to biological infestation such as from bacteria or fungi. Experimentally produced samples have gone for over 2 years without biological infestation or spoilage.

Branching is particularly useful as it facilitates increased molecular weight of the glycerol-based polyols and constructs structured polyols thereof. As described in US Published Application 2009/0130006 A1 branched glycerol-based polyols are capable of reducing scales in Bayer liquor during aluminum processing. As described in U.S. patent application Ser. No. 12/499,916, the glycerol-based polyols effectively increase brightness and whiteness of coated paper substrate without being frustrated by greening effect.

In at least one embodiment the inventive method comprises particular concentration of a strong base as the catalyst under a particular distillation environment at high reaction temperature for a desired reaction time. In at least one embodiment the strong base is CsOH, KOH, NaOH, any other strong base stronger than NaOH or any combination thereof in the amount of above 2%, preferably above 3%. In at least one embodiment the particular distillation environment is inert gas flow rates of more than 0.2 mol of inert gas per hour per mol of monomer used. In at least one embodiment the inert gas is nitrogen, carbon dioxide, any other inert gas, or any combination thereof. In at least one embodiment the particular distillation environment is a vacuum pressure of less than 760 mmHg. In at least one embodiment the reaction temperature is above 200 and below 300 degrees Celsius. In at least one embodiment the reaction temperature is from 230 to 260 degrees Celsius. The reaction is conducted over 2 hours to a number of hours as desired.

In at least one embodiment, the reaction produced polyols have a polydispersity of at least 1. In at least one embodiment, the reaction produced polyols have a polydispersity within the range of 1 to 30. For purposes of this application the term "polydispersity" is a term of art whose precise definition is provided in *Principles of Polymerization, 4th Edition*, by George Odion Wiley-InterScience (2004), Introduction pages 18-25.

The inventive method has a number of benefits. One advantage is the high proportion of valuable lactic acid or lactate salt present in the reaction product. In at least one embodiment, the lactic acid has been observed to be as much as at least 11% to 22% by weight of the reaction product. The produced lactic acid is particularly useful as it protects the polyglycerol from bacterial and fungal spoilage. Experimentally produced samples have gone for over 2 years without biological infestation or spoilage.

In at least one embodiment the degree of cyclization of the resulting polyol is 0.15 to 0.18.

In at least one embodiment, at least 30 to 35% of the produced polyglycerols are branched or hyperbranched polyglycerols. Branching or hyperbranching is particularly useful as it facilitates increased molecular weight of the polyglycerols. Furthermore as described in US Published Application 2009/0130006 A1 branched and hyperbranched polyglycerols are also capable of reducing scale in Bayer liquor during aluminum processing.

Without being limited to theory it is believed that the beneficial effects of the inventive process are a result of the unique conditions that the polymerization reaction occurs within. In prior art glycerol-based condensation polymerizations either no catalyst is used, weak bases or organic acid salts of alkaline metals are used, or a low catalyst loading of a strong base as the catalyst, typically from 0.1 to 2% is used. This results in linear or mostly linear glycerol-based polyols, and often low molecular weight glycerol-based polyols. In contrast the inventive process uses a higher amount of a strong base as the catalyst under a particular distillation environment to effectively produce the branched, cyclized glycerol-based polyols in a wide range of molecular weights with a beneficial co-product lactic acid or lactate as anti-biodegrading agent. Furthermore, the low reactivity atmospheric environment removes water that forms as a reaction byproduct, which prevents the water from inhibiting the polymerization reactions.

EXAMPLES

The foregoing may be better understood by reference to the following Examples, which are presented for purposes of illustration and are not intended to limit the scope of the invention:

A general procedure described here was followed by the examples. A reaction mixture of glycerol (500.0 parts) and a strong base in a particular amount (% by weight of active relative to the total weight of reaction solids) was stirred and gradually heated up to 230 to 260 degrees Celsius under particular inert gas flow rates. The reaction mixture was stirred at this temperature for a desired reaction time (in hours), and in-process samples were drawn after two or four hours and every one or two hours thereafter for product characterizations. Particular inert gas flow rates were applied starting from reaction time between 0 to 4 hours to the end of the reaction to remove water and possibly other volatiles from the reaction mixture and the condensation polymerization.

All samples in this invention were analyzed with a standard "borate" SEC method (size exclusion chromatography) and the reported molecular weights (MW) were weight average molecular weights based on calibration system of PEG/PEO narrow MW standards. For reaction time less than 8 hours the cut-off of integration limit was set right before the monomer glycerol (excluding glycerol), and for the reaction time at or greater than 8 hours the cut-off was set right before the co-product sodium lactate peak (excluding sodium lactate). The composition analyses were conducted by $^{13}$C NMR and GC-FID.

As shown in Tables 1, 2 and 3, a spectrum of unique desirable glycerol-based polyol products was produced through this invention. In Table 1 the molecular weights of polyglycerols increased efficiently with reaction time, and reached thousands of Daltons after reaction time of 8 hours.

TABLE 1

Molecular Weights of Polyglycerols Over Reaction Time*

| Rxn time, | Example 1 NaOH, 3.6% | | Example 2 KOH, 5.0% | | Example 3 CsOH, 12.3% | |
|---|---|---|---|---|---|---|
| hours | Cpd | MW | Cpd | MW | Cpd | MW |
| 4 | 1 | 185 | 8 | 330 | 12 | 300 |
| 6 | 2 | 430 | 9 | 650 | 13 | 690 |
| 8 | 3 | 2,500 | 10 | 2,100 | 14 | 3,500 |
| 10 | 4 | 3,600 | 11 | 3,000 | 15 | 5,900 |
| 12 | 5 | 6,200 | — | — | — | — |
| 14 | 6 | 7,800 | — | — | — | — |
| 16 | 7 | 9,100 | — | — | — | — |

*Cpd is a sample's or a compound's identity, and consistently used in other Tables 2 and 3.

TABLE 2

Composition Analysis by $^{13}$C NMR for Polyglycerols*

| Cpd | L % | DB |
|---|---|---|
| 1 | 2 | 0.15 |
| 2 | 6 | 0.24 |
| 3 | 10 | 0.30 |
| 4 | 14 | 0.32 |
| 5 | 15 | 0.34 |
| 6 | 13 | 0.34 |
| 7 | 13 | 0.33 |
| 8 | 8 | 0.21 |
| 9 | 12 | 0.29 |
| 10 | 14 | 0.31 |
| 11 | 14 | 0.32 |
| — | — | — |
| — | — | — |
| — | — | — |
| 12 | 7 | 0.21 |
| 13 | 12 | 0.29 |
| 14 | 15 | 0.33 |
| 15 | 16 | 0.34 |
| — | — | — |
| — | — | — |

*L %, determined as lactate (sodium) salt and calculated as lactic acid by weight; DB, degree of branching by mol fraction based on known literature method cited in the definition section.

TABLE 3

Analysis of Residual Glycerol by GC-FID*

| Cpd | Glycerol % |
|---|---|
| 2 | 5.1 |
| 4 | 0.2 |
| 9 | 2.9 |
| 11 | <0.1 |
| 13 | 2.3 |
| 15 | <0.1 |

*Glycerol determined by weight relative to the product solids on instrument HP 5890 Series II (column DB-wax, temperature program 60 to 250 degrees Celsius) and calibrated with pure glycerol.

In this invention the effects of the particular distillation environment on the molecular weights of polglycerols are shown in Table 4.

TABLE 4

Nitrogen Flow rate Dependence of Glycerol-based Polymerization*

| Rxn time Hours | Example 4 $N_2$ flow rate 0.19 MW | Example 5 $N_2$ flow rate 0.93 MW | Example 6 $N_2$ flow rate 1.86 MW | Example 7 $N_2$ flow rate 3.72 MW | Example 8 $N_2$ flow rate 7.45 MW |
|---|---|---|---|---|---|
| 8 | 570 | 1,200 | 2,100 | 3,100 | 4,100 |
| 10 | 730 | 2,200 | 3,500 | 6,400 | 6,700 |
| 16 | 1,200 | 4,700 | 6,800 | 9,300 | 6,700 |

*Unit of nitrogen flow rate is mol of nitrogen gas per hour for per mol of monomer or monomers; the reaction conditions for all examples are identical except the nitrogen flow rate (3.6% NaOH used).

The produced polyol's resistance to biological spoilage was proven with the following experiment:

Turbid cell suspensions in TSB were prepared for bacterial cultures and 0.5 ml of this cell suspension was inoculated into 10 mL of the produced polyol solutions. Final cell density in the inoculated products were estimated at approximately $5 \times 10^6$ cfu/ml. A spore suspension in phosphate buffer was used for the fungal isolate and 0.5 mL of the spore suspension was inoculated into 10 mL of the product samples. Final spore density in the inoculated product sample was estimated at approximately $5 \times 10^4$ spores/mL. Viability of the test cultures was confirmed by inoculation of 0.5 mL of the cell/spore suspensions into 10 mL TSB. No growth was observed in inoculated product samples (Table 5). In order to confirm the cultures were not viable, 0.1 mL of inoculated product samples was plated on TGE agar for bacterial test isolates and PDA for the fungal test isolate. The results proved that these polyol products do not readily support growth/viability of bacteria or fungi.

TABLE 5

Examination of inoculated media/product samples after 7-day incubation at room temperature.

| Test Medium | B. cereus | P. aeruginosa | K. pneumoniae | PAE Fungus |
|---|---|---|---|---|
| TSB Control | Growth | Growth | No growth | Growth |
| Polyol Product | No growth | No growth | No growth | No growth |
| Polyol Product | No growth | No growth | No growth | No growth |

TABLE 6

Observations of growth on TGE/PDA with inoculated product samples after 5-day incubation at room temperature.

| Test Medium | B. cereus | P. aeruginosa | K. pneumoniae | PAE Fungus |
|---|---|---|---|---|
| Polyol Product | No growth | No growth | No growth | No growth |
| Polyol Product | No growth | No growth | No growth | No growth |

While this invention may be embodied in many different forms, there are shown in the drawings and described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and incorporated herein.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), end ending with a maximum value of 10 or less, (e.g. 2.3 to 9.4, 3 to 8, 4 to 7), and finally to each number 1, 2, 3, 4, 5, 6, 7, 8, 9, and 10 contained within the range.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of synthesizing glycerol-based polyol products comprising the step of:
    reacting a reaction mass comprising at least glycerol monomer in the presence of a strong base catalyst of a concentration of above 2%, in a low reactivity atmospheric environment at a temperature above 200 degrees C. which produces a product comprising branched, cyclic polyols and a co-product comprising lactic acid, lactic salt, and any combination thereof and the co-product is in such a concentration that the polyol product is resistant to biological contamination for at least two years after synthesis, wherein the low reactivity atmospheric environment is a flow of an inert gas and the flow is at a rate of 0.93 to 3.72 mol of inert gas per hour per mol of monomer(s).

2. The method of claim 1 further comprising the steps of providing a catalyst above 3%.

3. The method of claim 2 in which the catalyst is selected from the group consisting of: NaOH, KOH, CsOH, a base stronger than NaOH, and any combination thereof.

4. The method of claim 1 in which the atmospheric environment is an atmospheric pressure of less than 760 mm Hg.

5. The method of claim 1 in which the glycerol-based polyol products are selected from the group consisting of polyglycerols, polyglycerol derivatives, a polyol having both glycerol monomer units and non-glycerol monomer units and any combination thereof the polyols have at least two hydroxyl groups.

6. The method of claim 1 in which at least a portion of the produced polyols have both at least a 0.1 degree of branching and at least a 0.01 degree of cyclization.

7. The method of claim 1 in which the co-product is at least 1% by weight.

8. The method of claim 1 in which the glycerol-based polyol products are at least 166 Daltons in molecular weight.

9. The method of claim 1 in which the glycerol-based polyol products have a polydispersity of at least 1.

10. The method of claim 1 in which the glycerol is pure, technical, crude, or any combination thereof.

11. The method of claim 1 further comprising other monomers selected from the group consisting of polyols and amines.

12. The method of claim 1 further comprising the steps of pre-determining the desired molecular weight of the produced polyglycerol and adjusting the atmospheric environment to match the environment optimum for producing the desired molecular weight.

13. The method of claim 1 further comprising the steps of pre-determining the desired degree of branching and the desired degree of cyclization of the produced polyglycerol and the desired amount of co-product, and adjusting the atmospheric environment to match the environment optimum for producing the desired degree of branching, degree of cyclization and amount of co-product lactic acid and/or lactate salt.

14. The method of claim 1 in which the branched, cyclic polyols are in molecular weight range of 2,240 to 150,000 Daltons and have a polydispersity range of 1 to 30.

15. The method of claim 1 in which the resulting polymer undergoes such an exothermic reaction that it becomes so crosslinked as to have a degree of branching greater than 0.2.

16. The method of claim 1 in which the resulting polymer is so crosslinked as to have a degree of branching greater than 0.2.

17. A method of synthesizing glycerol-based polyol products comprising the step of:
reacting a reaction mass comprising at least glycerol monomer in the presence of a strong base catalyst of a concentration of above 2%, in a low reactivity atmospheric environment at a temperature above 200 degrees C. which produces a reaction product comprising a polyol having a degree of branching greater than 0.2 and a co-product comprising lactic acid, lactic salt, and any combination thereof and the co-product is in such a concentration that the reaction product is resistant to biological contamination for at least two years after synthesis, wherein the low reactivity atmospheric environment is a flow of an inert gas and the flow is at a rate of 0.19 0.93 to 3.72 mol of inert gas per hour per mol of monomer(s).

18. A method of synthesizing glycerol-based polyol products comprising the step of:
reacting a reaction mass of glycerol monomer in the presence of a strong base catalyst of a concentration of above 2%, in a low reactivity atmospheric environment at a temperature above 200 degrees C. which produces a polyglycerol product comprising branched, cyclic polyols and a co-product comprising lactic acid, lactic salt, and any combination thereof and the co-product is in such a concentration that the polyol product is resistant to biological contamination for at least two years after synthesis, wherein the low reactivity atmospheric environment is a flow of an inert gas and the flow is at a rate of 0.93 to 3.72 mol of inert gas per hour per mol of monomer(s).

19. The method of claim 1, wherein the lactic acid is present in an amount from 11% to 22% by weight of the reaction product.

* * * * *